United States Patent [19]

Sievert

[11] Patent Number: 5,406,008

[45] Date of Patent: Apr. 11, 1995

[54] PROCESS FOR THE MANUFACTURE OF HYDROFLUOROCARBONS

[75] Inventor: Allen C. Sievert, Elkton, Md.

[73] Assignee: E. I. Du Pont de Nemours and Company, Wilmington, Del.

[21] Appl. No.: 461,474

[22] Filed: Dec. 28, 1989

[51] Int. Cl.$^6$ .............................................. C07C 19/08
[52] U.S. Cl. ...................................... 570/123; 570/175
[58] Field of Search .................................. 570/123, 175

[56] References Cited

U.S. PATENT DOCUMENTS

| | | |
|---|---|---|
| 3,346,652 | 10/1967 | Pilipovich . |
| 4,158,023 | 6/1979 | von Halasz . |
| 4,258,225 | 3/1981 | Feiring . |
| 4,311,863 | 1/1982 | Gumprecht . |
| 4,330,475 | 5/1982 | Adcock et al. . |
| 4,377,715 | 3/1983 | Nychka et al. ............ 570/175 |
| 4,513,154 | 4/1985 | Kurtz . |
| 4,754,085 | 6/1988 | Geruasutti et al. ........ 570/175 |
| 4,937,398 | 6/1990 | Tung et al. ............... 570/175 |

FOREIGN PATENT DOCUMENTS

| | | |
|---|---|---|
| 31519 | 7/1981 | European Pat. Off. . |
| 31210 | 11/1984 | European Pat. Off. . |
| 187643 | 7/1986 | European Pat. Off. . |
| 219823 | 4/1987 | European Pat. Off. . |
| 64-38034 | 2/1989 | Japan . |

OTHER PUBLICATIONS

Henne, Organic Reactions, vol. 2, p. 56 (1944).
Henne et al., J. Am. Chem. Soc. vol. 58, p. 404 (1936).
McBee et al., Ind. Eng. Chem. vol. 39, p. 409 (1947).
Calfee et al., J. Am. Chem. Soc. vol. 62, p. 27 (1939).
Miller, J. Am. Chem. Soc. vol. 62, p. 341 (1940).
Fox et al., J. Electrochem. Soc. vol. 118, p. 1246 (1971).
Nagase et al., Bull. Chem. Soc. Japan vol. 40, p. 2358 (1967).
Maxwell et al., J. Am. Chem. Soc. vol. 82, p. 5827 (1960).
Calfee et al., J. Am. Chem. Soc. vol. 59, p. 2072 (1937).
Calfee et al., J. Am. Chem. Soc. vol. 61, p. 3552 (1939).
Young et al., J. Am. Chem. Soc. vol. 62, p. 1171 (1940).
Cadman et al., Faraday Trans. I vol. 72, p. 1428 (1976).
Tedder, Chemistry and Industry p. 508 (1955).
Miller et al., J. Am. Chem. Soc. vol. 79, p. 3084 (1957).
Burdon et al., Tetrahedron, vol. 32, p. 1041 (1976).
Holub et al., J. Am. Chem. Soc. vol. 72, p. 4879 (1950).
Sheih et al., J. Org. Chem. vol. 35, p. 4020 (1970).
Rausch et al., J. Org. Chem. vol. 28, p. 494 (1963).
Henne et al., J. Am. Chem. Soc. vol. 58, p. 889 (1936).
Henne et al., J. Am. Chem. Soc. vol. 67, p. 1906 (1945).
Conte et al., J. Fluorine Chem., vol. 48, p. 319 (1988).
Adcock et al., J. Org. Chem., vol. 48, p. 4953 (1983).
Adcock et al., J. Org. Chem., vol. 49, p. 2719 (1984).

*Primary Examiner*—Alan Siegel

[57] ABSTRACT

A process for the manufacture of hydrofluorocarbons by the reaction of selected relatively low modular weight saturated and unsaturated hydrocarbons and corresponding partially halogenated hydrocarbons with elemental fluorine in the vapor phase. By selecting the ratio of $F_2$/ substrate in combination with reaction temperature and reactor residence time the extent of fluorination of a substrate and degree of overfluorination can be controlled. Thus, starting with 1,1,1-trifluoroethane, $CH_3CF_3$ (HFC-143a), 1,1,1,2-tetrafluoroethane, $CH_2FCF_3$ (HFC-134a) is produced by simple thermal fluorination even in the presence of simultaneous formation of pentafluoroethane HFC-125. The use of compounds highly reactive toward fluorine are shown to promote the selective fluorination of partially fluorinated substrates.

8 Claims, 1 Drawing Sheet

PROCESS FOR THE MANUFACTURE OF HYDROFLUOROCARBONS

BACKGROUND OF THE INVENTION

1. Field of the Invention

This invention relates to a process for the manufacture of hydrofluorocarbons (HFC's) by the reaction of hydrocarbons or fluoro-substituted hydrocarbons with elemental fluorine in the vapor phase.

2. Description of the Prior Art

Chlorofluorocarbons (CFC's) such as $CF_2Cl_2$ (CFC-12) are used in industry as refrigerant fluids in heat pumps and compressors. There exists a need to replace CFC-12 and related materials with a compound that does not have a prolonged residence time in the atmosphere. Hydrofluorocarbons (HFC's) are compounds containing only carbon, hydrogen, and fluorine atoms. Certain members of this class of compounds, such as $CH_2FCF_3$ (HFC-134a) and $C_2HF_5$ (HFC-125), possess the physical properties that allow them to replace products currently in use which are suspected of depleting stratospheric ozone. For example, HFC-134a is now known to be a suitable replacement for CFC-12, and HFC-125 can be used as a propellant and working fluid. Since many of these compounds are not items of commerce, and cannot be synthesized by procedures known in the art, there is a need for new procedures to manufacture these compounds on a commercial scale.

As disclosed in "Organic Fluorine Chemistry" by W. A. Sheppard and C. M. Sharts (W. A. Benjamin, Inc., New York, 1969), fluorinated compounds are typically prepared by the reaction of chloroalkanes or chloroolefins with HF in the liquid or vapor phase usually in the presence of catalysts such as halogen compounds of antimony. It has long been recognized in the art (see, for example, A. L. Henne, *Organic Reactions*, Vol. 2, p. 56 (1944)) that conversion of —$CHCl_2$ and —$CH_2Cl$ groups to —$CHF_2$ and —$CH_2F$ groups is very difficult to achieve using these standard reaction procedures.

For example, Henne, et al. (*J. Am. Chem. Soc.*, Vol. 58, pp. 404–406 (1936)) report the conversion of $CH_2ClCCl_3$ to $CH_2ClCClF_2$ (HCFC-132b) using an antimony catalyst. In another case, McBee (Industrial and Engineering Chemistry, Vol. 39, pp. 409–412 (1947)) described the reaction of trichloroethylene with HF in the presence of an antimony catalyst to give $CF_3CH_2Cl$ (HCFC-133a) and HCFC-132b. The conversion of trichloroethylene to HCFC-133a is also described in British Patent No. 1,585,938 where it is stated that no tetrafluoro compounds were observed. U.S. Pat. No. 4,311,863 pointed out the difficulty of converting HCFC-133a to $CF_3CH_2F$ (HFC-134a) which requires high temperatures and special alkali metal fluoride catalysts. U.S. Pat. No. 4,851,595 teaches that HCFC-133a may also be converted to HFC-134a via $SbF_5$, a very powerful fluorinating agent; however, conversions were low and contact times were high. In European Patent Application No. 187,643 a tin-based catalysts system is described wherein trichloroethylene is converted to a mixture of HCFC-132b and $CH_2ClCCl_2F$ (HCFC-131a). Similar results were disclosed in U.S. Pat. No. 4,258,225 using a $TaF_5$ catalyst. This reference also taught that perchloroethylene and HF react in the presence of $TaF_5$ to form a mixture of $CHCl_2CCl_2F$ (HCFC-121) and $CHCl_2CClF_2$ (HCFC-122); in this case the —$CHCl_2$ group is resistant to substitution by fluoride.

As can be seen from this prior art, the well-known process of exchange of chlorine for fluorine severely limits the scope of compounds that can easily be prepared; —$CH_2Cl$ and —$CHCl_2$ groups are predominant hydrogen-containing functionalities in compounds that can be attained by this technique.

An alternative approach to HCFC's is the chlorination of fluorocarbons such as $CH_3CF_3$ (HFC-143a). For example, McBee (*Industrial and Engineering Chemistry*, Vol. 39, pp. 409-412 (1947)) reported that vapor phase chlorination of HFC-143a afforded a mixture of HCFC-133a, HCFC-132b, $CHCl_2CF_3$ (HCFC-123), and the fully chlorinated $CF_3CCl_3$ (CFC-113a). McBee also reported the chlorination of $CH_3CClF_2$ (HCFC-142b) to give HCFC-132b, HCFC-122, and the fully chlorinated $CClF_2CCl_3$ (CFC-112a). Again, using this technique —$CH_2Cl$ and —$CHCl_2$ groups dominate the attainable substitution pattern.

HFC's have also been prepared by direct fluorination processes using elemental fluorine. Early work in this field by Calfee, et al. (*J. Am. Chem.* Vol. 62, pp. 267–269 (1939)) demonstrated that ethyl chloride could be fluorinated in the gas phase to a mixture of $CF_4$, $CF_3Cl$, $CF_3CF_2Cl$, $CF_2=CCl_2$, and $CHF_2CH_2Cl$. Miller (*J. Amer. Soc.*, Vol. 62, pp. 341–344 (1940)) and Bockemueller (*Ann.* Vol. 506, p. 20 (1933)) reported the fluorination of highly chlorinated alkanes and olefins in the liquid phase to give perhalogenated compounds as well as some higher chloroalkanes.

Fluorinated hydrocarbons have also been made electrochemically. For example, Fox et al. (*J. Electrochem. Soc. Electrochem. Technology*, Vol. 118, pp. 1246–1249, 1971) reported the electrochemical fluorination of ethane and found that mixtures of fluorinated ethanes were produced. The tetrafluoroethane fraction always contained both $CHF_2CHF_2$ (HFC-134) and HFC-134a with the former predominating. Similarly, mixtures of HFC's and HCFC's were obtained by Nagase, et al. (*Bulletin of the Chemical Soc. of Japan*, Vol. 40, pp. 2358–2362, 1967) when ethane or ethylene were fed into an electrochemical cell with a source of chlorine such as $Cl_2$, phosgene, or chlorocarbons. Again the tetrafluoroethane fraction contained relatively equal amounts of HFC-134 and HFC-134a.

In a series of papers, Calfee, et al. (*J. Am. Chem. Soc.*, Vol. 59, pp. 2072–2073, 1937; and Vol. 61, pp. 3552–3554, 1939), Young, et al. (*J. Am. Chem. Soc.*, Vol. 62, pp. 1171–1173, 1940), and Maxwell, et al. (*J. Am. Chem. Soc.*, Vol. 82, pp. 5827–5830, 1960) the fluorination of ethane is reported in a variety of fluorination reactors. Although mixtures of fluorinated ethanes were obtained including HFC-134, HFC-134a was not mentioned as a product from these reactions. Cadman, et al. (*Transactions of the Faraday Soc.*, Vol. 72, pp. 1428–1440, 1976) have studied the fluorination of ethanes and HFC's but this work was carried out at extremely low conversion.

Elemental fluorine has also been used to make perfluorinated compounds. For example, in U.S. Pat. No. 4,158,023 a two-step process is claimed for making perfluoropropane, $C_3F_8$, by treating $CF_2=CFCF_3$ with HF followed by perfluorination to $C_3HF_7$. European Patent Applications 31,519 and 32,210 and U.S. Pat. No. 4,377,715 also disclose and claim processes for perfluorinated compounds. The goal of these investigations has been the preparation of perfluorinated compounds for which elemental fluorine is considered to be well-suited.

It is well known in the art that fluorinations of aliphatic compounds with elemental fluorine can be accelerated by the use of ultraviolet light (e.g., see J. M. Tedder, *Chemistry and Industry*, Apr., 30, 1955, pp. 508-509). Very little use appears to have been made of chemical initiators for direct fluorinations. For many fluorinations this is not necessary due to the high degree of reactivity of fluorine with many substrates; however, direct fluorination of partially fluorinated materials often requires higher temperatures for acceptable conversions. Miller, et al. (*J. Am. Chem. Soc.*, Vol. 79, pp. 3084-3089, 1957) reported the preparation of $CCl_3CClFCClF_2$ from $CHCl_3$ and $CClF=CClF$ by co-feeding fluorine; however, none of the chloroform fluorination product, $CFCl_3$, was apparently produced.

Another means of preparing HFC's known in the art is the reaction of saturated or unsaturated hydrocarbons and fluorinated hydrocarbons with metal fluoride compounds. For example, Burdon, et al. (*Tetrahedron*, Vol. 32, pp. 1041-1043, 1976) has reported that ethane or ethylene react with cobalt trifluoride to form a mixture of fluorinated ethanes. Again HFC-134a was a minor product along with somewhat greater amounts of HFC-134. Holub, et al. (*J. Am. Chem. Soc.*, Vol. 72, pp. 4879-4884, 1950) reported that $CHF_2CH_2F$ (HFC-143) could be fluorinated to a mixture of HFC-134 and HFC-125. Shieh, et al. (*J. Organic Chem.*, Vol. 35, pp. 4020-4024, 1970) have reported that ethylene can be converted to a mixture of fluorinated ethanes using $XeF_4$ but tetrafluoroethanes were not produced.

Rausch, et al. (*J. Organic Chem.*, Vol. 28, 494-497, 1963) has used cobalt trifluoride and related metal fluorides to convert vinylidene fluoride to HFC-134a. In U.S. Pat. No. 3,346,652 boron trifluoride and trifluoroamine oxide were used to prepare HFC-134a from vinylidene fluoride. Both of these techniques required exotic reagents to prepare HFC-134a.

SUMMARY OF THE INVENTION

The present invention provides a process for the thermal fluorination of selected relatively low molecular weight saturated and unsaturated hydrocarbons and corresponding partially halogenated hydrocarbons by a vapor phase reaction with elemental fluorine. The extent of fluorination of the selected substrate according to the present invention is predominantly controlled by the ratio of fluorine to substrate fed to the vapor phase reactor. Thus, according to the present invention performing the fluorination reaction such that fluorine is the limiting reactant allows for the substitution of one hydrogen in a substrate by one fluorine atom to be the dominant reaction scheme. It has been further discovered according to the present invention that the intentional presence of a small amount of a compound which is highly reactive towards fluorine initiates the vapor phase fluorination of partially fluorinated substrates.

Thus, the present invention provides a process for preparing hydrofluorocarbons comprising the steps of:
(a) contacting a compound selected from the group consisting of:
(i) saturated $C_1$ to $C_5$ hydrocarbons,
(ii) unsaturated $C_2$ to $C_5$ hydrocarbons,
(iii) saturated, partially fluorinated $C_1$ to $C_5$ hydrocarbons wherein the saturated, partially fluorinated hydrocarbon contains fewer fluorine atoms than are to be present in the hydrofluorocarbon to be prepared, and
(iv) unsaturated, partially fluorinated $C_2$ to $C_5$ hydrocarbons wherein the unsaturated, partially fluorinated hydrocarbon contains fewer fluorine atoms than are to be present in the hydrofluorocarbon to be prepared with an effective amount of fluorine in the vapor phase for sufficient time to produce a hydrofluorocarbon; and
(b) recovering the hydrofluorocarbon produced in step (a).

It is an object of the present invention to provide a process for the manufacture of partially fluorinated hydrocarbons by reacting a substrate with elemental fluorine in the vapor phase. It is a further object of the present invention to provide such a vapor phase fluorination process wherein the formation of by-products which are more highly fluorinated than the desired products is minimized. It is a further object of this invention to provide a process for the manufacture of 1,1,1,2-tetrafluoroethane, $CF_3$—$CH_2F$ (HFC-134a), which does not involve the troublesome conversion of $CH_2ClCF_3$ in the final step. It is a further object of this invention to provide a process for the manufacture of HFC-134a which involves the use of the readily available precursor 1,1,1-trifluoroethane, $CH_3CF_3$ (HFC-143a). It is a further object of this invention to provide a process for the manufacture of HFC-134a in which the final product is substantially free of the isomer 1,1,2,2-tetrafluoroethane, $CHF_2CHF_2$ (HFC-134) and other unwanted by-products. It is a further object of this invention to provide a process for the manufacture of HFC-134a in which pentafluoroethane, $C_2HF_5$ (HFC-125), is produced as a useful co-product. It is a further object of this invention to provide a process for the co-manufacture of HFC-134, HFC-134a and HFC-125. It is a further object of this invention to provide a process for the production of partially and fully fluorinated compounds in which the fluorination of partially fluorinated substrates is promoted by the addition of saturated and unsaturated hydrocarbons, saturated and unsaturated alkyl halides (halide=Cl, Br, I), partially halogenated olefins (halogen=F, Cl, Br, I), and $CF_3I$.

BRIEF DESCRIPTION OF THE DRAWING

The Figure schematically illustrates a gas phase reactor system according to the present invention.

DESCRIPTION OF THE PREFERRED EMBODIMENTS

The thermal fluorination process according to the present invention generally involves the reaction of selected substrates with elemental fluorine in the vapor phase under conditions that avoid many of the problems associated with prior art processes. The substrate to be fluorinated by the vapor phase method according to the present invention is typically a $C_1$ to $C_5$ saturated or $C_2$ to $C_5$ unsaturated hydrocarbon or corresponding partially fluorinated hydrocarbon. Preferably the invention involves reacting saturated, hydrocarbons (HFC's) of the general formula:

$$C_nH_{2n+2-m}D_m$$

where n=1, 2, 3, 4, or 5 and $$0 \leq m < 2n+2$$

with elemental fluorine in the vapor phase to give HFC's of the general formula:

$$C_nH_{2n+2-p}F_p$$

where $m < p \leq 2n+2$ and m-and n are as defined above;

and reacting unsaturated, hydrocarbons of the general formula:

$$C_aH_{2a-b}F_b$$

where a=2, 3, 4, or 5 and $$0 \leq b \leq 2a$$

with elemental fluorine in the vapor phase to give HFC's of the general formula:

$$C_aH_{2-b-c}F_{b+2+c}$$

where $(b+2+c) \leq (2a+2)$, and a, b are as defined above;

and reacting saturated, cyclic hydrocarbons of the general formula:

$$C_iH_{2i-j}F_j$$

where i=3, 4, 5 or 6, and $$0 \leq j < 2i$$

with elemental fluorine in the vapor phase to give HFC's of the general formula:

$$C_iH_{2i-k}F_k$$

where $j < k \leq 2i$ and i and j are as defined above;

and reacting unsaturated, cyclic hydrocarbons of the general formula:

$$C_gH_{2g-2-h}F_h$$

where g=3, 4, 5 or 6 and $$0 \leq h \leq (2g-2)$$

with elemental fluorine in the vapor phase to give HFC's of the general formula:

$$C_gH_{2g-2-h-e}F_{h+2+e}$$

where $(h+2+e) \leq 2g$ and g and h are as defined above.

Thus, the process according to the present invention provides, by way of example but not limited to, for the conversion of $CH_2F_2$ to $CHF_3$, $CHF_2CHF_2$ to $C_2HF_5$, $CHF_2CF_2CH_2F$ to $CHF_2CF_2CHF_2$, $CF_3CHFCH_3$ to $CF_3CHFCH_2F$, $CF_3CF_2CH_2F$ to $CF_3CF_2CHF_2$, $CH_3CF_2CF_2CH_3$ to $CHF_2CF_2CF_2CHF_2$, Cyclo-$CF_2CF_2CH_2CH_2$ to cyclo-$CF_2CF_2CHFCHF$, $C_2H_4$ to $CH_2FCH_2F$, $CF_3CH=CH_2$ to $CF_3CHFCH_2F$, $C_2H_6$ to a mixture of $C_2H_5F$, $CH_2FCH_2F$, $CH_3CHF_2$, $CH_2FCHF_2$, and $CH_3CF_3$, or $C_2H_6$ to a mixture of $CH_2FCFH_2$, $CH_3CF_3$, $CHF_2CHF_2$, $CH_2FCF_3$, $C_2HF_5$ and $C_2F_6$. Preferably the process according to the present invention provides for the conversion of $C_2HF_5$ to $C_2F_6$, the conversion of $CH_2=CF_2$ to $CH_2FCF_3$, the conversion of $CHF=CHF$ to $CHF_2CHF_2$, and the conversion of $CH_2FCHF_2$ to a mixture of $CHF_2CHF_2$ and $CH_2FCF_3$. Most preferably the process provides for the conversion of $CH_3CF_3$ to $CH_2FCF_3$. Furthermore, these conversions may be carried out using the process of this invention in such a way that the formation of by-products which are more highly fluorinated than the desired products is minimized although it is difficult to eliminate by-products entirely.

The starting materials (i.e., the substrates to be fluorinated) for carrying out the process of the present invention can be prepared by any of the processes generally known to those skilled in the art. For example, (but again not by way of limitation) a convenient starting material for the preparation of 1,1,1,2-tetrafluoroethane, $CH_2FCF_3$ (HFC-134a) is 1,1,1-trifluoroethane, $CH_3CF_3$ (HFC-143a). HFC-143a has been prepared by the reaction of methyl chloroform, $CH_3CCl_3$, with HF in the presence of an antimony catalyst (Henne, et al., *J. Am. Chem. Soc.*, Vol. 58, pp 889-890, 1936). In addition, McBee, et al., (*Industrial and Engineering Chemistry*, Vol. 39, pp. 409-412 (1947)) have reported the reaction of 1,1-dichloroethylene with HF to form $CH_3CCl_2F$ (HCFC-141b), $CH_3CClF_2$ (HCFC-142b), and $CH_3CF_3$ (HFC-143a) in ratios that vary depending on the amount of HF added to the reaction.

With respect to the above mentioned most preferred conversion, it is well known in the art that a $CF_3$ group deactivates the hydrogen atom of an adjacent —$CH_2R$ (R=alkyl or substituted alkyl) or —$CH_3$ group with respect to halogenation (for example, see Henne, et al., *J. Am. Chem. Soc.*, Vol. 67, pp 1906-1908, (1945) and references therein). For example, in the case of thermal chlorination of $CH_3CF_3$ reported by McBee, et al., (*Industrial and Engineering Chemistry*, Vol. 39, pp. 409-412 (1947)), even at a $CH_3CF_3$ conversion of only about 49%, substantial amounts of the higher chlorination products, $CHCl_2CF_3$ and $CCl_3CF_3$, were formed in addition to the desired $CH_2ClCF_3$. Hence, even though $CH_3CF_3$ underwent chlorination with difficulty, chlorination of $CH_2ClCF_3$ and $CHCl_2CF_3$ proceeded relatively rapidly. In view of this, the observed formation of HFC-134a in the presence of simultaneous formation of HFC-125 by a relatively simple and straight forward vapor phase thermal fluorination process of the present invention should be considered a truly unexpected result.

The extent of fluorination of a substrate obtained as a result of the process of the present invention is determined to a large degree by the ratio of fluorine to substrate fed to the reactor. The $F_2$/substrate ratio may vary between about 0.1 and about 10 if one hydrogen of the substrate is to be replaced by a fluorine atom. Higher ratios of $F_2$/substrate may be desirable if more than one hydrogen is to be replaced with a fluorine atom. In the case of fluorination of HFC-143a to form HFC-134a, it is preferred that the $F_2$/HFC-143a ratio be kept below about 10. $F_2$/HFC-143a ratios higher than about 10 will result in an unacceptable degree of overfluorination to HFC-125 and FC-116 or will result in a large amount of fluorine being scrubbed or recycled to the reactor.

In general, with temperature held constant increasing the $F_2$/substrate ratio will drive the fluorination reaction to a higher percent conversion of the substrate as illustrated later for the conversion of HFC-143a to HFC-134a in Examples 1 through 3 and as shown in Table I. However, as the conversion is increased, the extent of overfluorination also increases if the rate of fluorination of the product is competitive with the rate of fluorination of the starting material as is the case for HFC-143a. Thus, Examples 1 through 3 illustrate that the ratio of HFC-134a to HFC-125 decreases as the conversion of the HFC-143a increases.

In general it is preferred to run the fluorination reactions in such a way that fluorine is the limiting reactant. Hence, for substitution of one hydrogen in a substrate by one fluorine atom as in the case of conversion of HFC-143a to HFC-134a, it is preferred to use an $F_2$/HFC-143a ratio that is less than one. This maximizes the conversion of fluorine which is the more expensive of the two starting materials and results in less fluorine being scrubbed or recycled to the reactor. In addition, it is preferred that the ratio of $F_2$/substrate be greater than about 0.1 so that a reasonable conversion of substrate be obtained in the reactor. Operating the process of the invention at a $F_2$/HFC-143a ratio less than one enables the fluorination to be run at higher temperatures than would be practical with ratios greater than one (see Examples 6 through 9 and Table I).

The optimum temperature for operating the process of this invention is dictated by the reactivity of the substrate with fluorine, the desired conversion of the substrate in one pass through the fluorination zone, the desired selectivity of the fluorination, the ratio of $F_2$ to substrate employed, and the physical properties of the substrate (e.g., boiling point). Since the process of this invention is run in the vapor phase, it is preferred that the temperature of the reactor be above the dew points of the substrate, intermediates, and products of the reaction so as to eliminate the possibility of condensation of material in the reactor. In a very broad sense the process of the invention may be carried out between temperatures of $-80°$ C. and $+200°$ C. In the case of the fluorination of HFC-143a, it is preferred to run the fluorination above about 60° C. and below about 200° C. At lower temperatures, the conversion of HFC-143a is minimal even with an excess of fluorine, and at higher temperatures the selectivity of the process is in general too low. Examples 3 through 5 in Table I illustrate that increasing the reaction temperature at a constant ratio of $F_2$ to HFC-143a results in substantially increased HFC-143a conversion but with a concomitant loss of selectivity as measured by a reduction in the HFC-134a to HFC-125 ratio. Examples 6 through 9 in Table I show that the same principle applies in cases where the ratio of $F_2$ to HFC-143a is less than 1. In this case the conversions of HFC-143a rival that obtained at low temperatures with a large excess of $F_2$.

In general the higher the reactivity of the substrate, the lower the fluorination temperature that may be used. The reactivity of a substrate toward fluorine is determined, in part, by the amount of hydrogen in the molecule. The larger the amount hydrogen relative to fluorine the more reactive the molecule is likely to be with respect to elemental fluorine. Hence, $C_2H_6$ is substantially more reactive toward fluorine than is $CH_3CF_3$. The former can be completely converted to fluorinated products at $-50°$ C. with two equivalents of fluorine (see Example 28) whereas the latter undergoes only about 2% conversion at 88° C. with 2.5 equivalents of fluorine (see Example 1). However, there will be some variation in reactivity of isomeric species depending on the pattern of substitution. For example, $CH_3CF_3$ is substantially less reactive toward fluorine than is the isomer, $CH_2FCHF_2$ owing to the deactivating effect of an adjacent —$CF_3$ group mentioned above (see Example 27 and Table V).

The residence time of the substrate in the fluorination zone coupled with the $F_2$/substrate ratio, the reactor temperature, and the reactivity of the substrate will determine the extent of fluorination of the substrate that occurs during the reaction. The optimum residence time will also depend to a great extent on the reactor configuration and the desired degree of conversion of the substrate to product in a single pass through the reactor. In general, the longer the residence time of the substrate in the reactor, the greater the degree of conversion of the substrate to products will occur. However, further conversion with greater residence time in the fluorination zone will not occur if the fluorine fed to the reactor becomes consumed before the substrate and products exit the reactor. This is particularly likely to occur if fluorine is the limiting reagent as is the case in the preferred mode for the process of this invention.

It is well known in the art that even small amounts of ultraviolet light can noticeably promote fluorinations; this has been used particularly in cases where perfluorinated materials are desired. However, selective fluorinations of partially fluorinated compounds can be rather slow reactions; for example, the conversion of HFC-143a to HFC-134a. According to the present invention it has been found that co-feeding the partially-fluorinated substrate with compounds that are highly reactive toward fluorine initiates the reaction. Compounds that are acceptable as initiators for fluorination reactions include saturated and unsaturated hydrocarbons, for example, $CH_4$, $C_2H_6$, $C_3H_8$, $C_2H_4$, or $C_3H_6$; alkyl halides (halide=Cl, Br, I), for example, $CH_3Cl$, $C_2H_5Cl$, $CH_3Br$, or $CH_3I$; halo-substituted olefins (halide=F, Cl, Br, I), for example, $CH_2=CF_2$, $CH_2=CCl_2$, cis- or trans-$CHCl=CHCl$, $CHCl=CCl_2$, $CHF=CHCl$, or $CF_3CH=CH_2$; perfluoroalkyl iodides, for example, $CF_3I$ or $C_2F_5I$; and partially fluorinated alkanes that are significantly more reactive toward fluorine than the intended substrate. For example, for the conversion of $CH_3CF_3$ to $CH_2FCF_3$, $CH_2FCHF_2$ is an initiator (compare Examples 12 and 21) whereas $C_2HF_5$ would not be. Suitable initiators for vapor phase processes must have a sufficiently low boiling point that they are easily evaporated and have a dew point above the temperature of the fluorination zone. Inexpensive initiators such as $CH_4$, $C_2H_4$, or $C_2H_6$ are particularly useful.

In general acceptable concentrations of initiators are between about 0.1 mole % and about 10 mole % with the preferred concentrations between about 0.3 mole % and about 4 mole %. Lower concentrations of initiators are not sufficient to initiate the reaction while higher concentrations do not provide any additional benefit (compare Examples 13 with 14 and 17 with 18) but only serve to increase the amount of impurities in the product. $CH_2=CF_2$ is a particularly convenient initiator for the conversion of $CH_3CF_3$ to $CH_2FCF_3$ since $F_2$ addition to $CH_2=CF_2$ gives $CH_2FCF_3$ (see Example 10 through 16, 25, and 26). Comparison of Example 12, 13, 14, and 17 through 24 indicate that there is some difference in efficiency of a number of initiators and, surprisingly, some differences in the selectivity of the fluorination reactions. The Examples also show that the chemically-initiated reactions have conversion comparable to a photochemical fluorination.

Table IIa shows that the difference between a chemically-initiated and uninitiated reaction is more noticeable at lower temperatures than at higher temperatures. In addition the effect is more noticeable when fluorine is the limiting reagent in the reaction which is the preferred mode for using the process of this invention.

Since the intention of this process is often not to perfluorinate the substrate, elaborate reactors employing photochemical steps, extremely high temperatures, and high concentrations of fluorine are not required. The characteristics and features that are required for a reactor include, by way of example but not limited thereto: (i) sources of fluorine and carrier gas, (ii) a source of the substrate to be fluorinated, (iii) a means to measure and regulate the flow of reactants into the reactor, (iv) a fluorination zone, (v) a means of measuring and regulating the temperature of said fluorination zone, (vi) a way of collecting the product of the reaction, (vii) a way of separating the products from the unconverted substrate, and (vii) a means of scrubbing unreacted fluorine or a means of returning it to the reactor.

Fluorine gas to be used in the process according to the present invention may either be purchased commercially or generated as needed such as by the electrolysis of HF in a cell adjacent to the reactor by any of the processes well known in the art. The quality of the commercial grade material is usually adequate for the purposes of this invention so that further purification or removal of any HF present in the gas is not necessary. Carrier gases are typically employed in the fluorination process according to the present invention to reduce the extent of fluorination occurring in the reaction and to reduce the amount of unwanted by-products as well as to adjust the overall residence time of the substrate in the reactor by varying the total gas flow rate. Suitable carrier gases include helium, nitrogen, argon and the like. Although nitrogen is the least expensive carrier gas, helium is the preferred carrier gas if a liquid nitrogen trap is employed as a means of collecting the reaction products. The carrier gas is typically dried before entering the reactor by passing the gas through a water-extracting material such as molecular sieves, calcium sulfate or the like.

In order to control the extent or degree of fluorination that occurs in the reactor, the fluorine is preferably diluted with a carrier gas before entering the reactor. This can be conveniently accomplished by either purchasing commercial mixes of fluorine and a carrier, e.g., 5% fluorine in nitrogen, or by starting with pure fluorine gas and mixing it with the carrier gas in the concentration required for the most efficient operation of the invention. Preferably this is accomplished by combining measured flows of fluorine and helium in a mixing chamber which consists of a cylinder packed with a material such as copper turnings or the like to help intermix the gases. The gas flows entering the mixing chamber can be measured by means of rotometers or mass flowmeters of the type well known in the art.

Although the substrates of this invention are liquids or gases, low melting solids may also be used in the process of the invention particularly if they sublime at temperatures below about 150° C. If the substrate is a liquid, the carrier gas is used to carry it into the vapor phase by purging the carrier gas through a container of substrate to be fluorinated. Alternatively, the substrate may be continuously injected into a stream of the carrier gas, optionally heated, by means of a pump. If the substrate is a gas it is simply fed into the reactor through a rotometer. The substrate is optionally diluted with carrier gas to minimize the appearance of higher molecular weight by-products due to radical dimerization and other side reactions.

The volume percentage of fluorine present in the reactor will be dependent on the $F_2$/substrate ratio, the amount of carrier gas fed to the reactor, and the desired residence time in the reactor. Preferably, percentages of fluorine in the vapor phase will be in the range of about 3% to about 30%. Even lower percentages can be used if a photochemical process or a chemical initiator is employed. Attempts to use a high percent fluorine in the vapor phase while keeping the $F_2$/substrate ratio less than about 5 could result in large amounts of by-products due to radical recombination side processes.

The reactor to be used in the process according to the present invention may be any such reactor as generally known in the art including any simple tubular reactor. One particularly convenient type of reactor is described by Nychka, et al. in U.S. Pat. No. 4,377,715, herein incorporated by reference for descriptive purposes, wherein a porous inner tube within the reactor is used to introduce the mixture of fluorine and carrier gas to the reactor. This has the advantage of introducing the fluorine to the substrate over a distance within the reactor rather than at a point source. Introducing the reactants at a single point has the potential of causing a poorly controlled reaction between the fluorine and the substrate where the two gas streams meet. The reactor may be empty or packed with a material such as copper turnings or the like generally known in the art to provide favorable mixing of the gas streams, good dissipation of heat, and possibly even an active surface for heterogeneous reactions.

The process according to the present invention may be run either above or below atmospheric pressure. Preferably the process is operated at approximately atmospheric pressure with the only pressure above atmospheric being due to the back pressure of the system.

Since the selectivity of the reactions are temperature dependent, a means of cooling and heating the reactor should be provided. This may be accomplished by surrounding the reactor with heating or cooling coils or with an electric heating tape or by immersing the reactor in a heat transfer medium. If the latter procedure is followed, it is useful to use a heat transfer medium that it is compatible with fluorine in the event that a leak in the system develops.

The products of the reaction are preferably collected in a cold trap immersed in a bath such as liquid nitrogen or dry ice. If liquid nitrogen is used as the cooling agent care must be taken to avoid condensation of the carrier gas or unreacted fluorine. The condensed products are separated from the unreacted substrate by conventional means used in the art such as by a Podbielniak still or by trap-to-trap distillation on a vacuum line. The products of the reaction may also be separated as they emerge from the reactor by means of a series of cold traps each at successively lower temperatures.

Unreacted fluorine emerging from the reactor is preferably scrubbed by means of a trap containing soda lime, alumina, or charcoal. Commercially, the process of this invention would preferably be operated in such a way that either the fluorine conversion is high or unreacted fluorine is returned to the reactor. High fluorine conversion is attained by using a plurality of reactors in which the fluorine-containing effluent from a reactor is combined with more substrate in a second fluorination zone.

Figure 1:
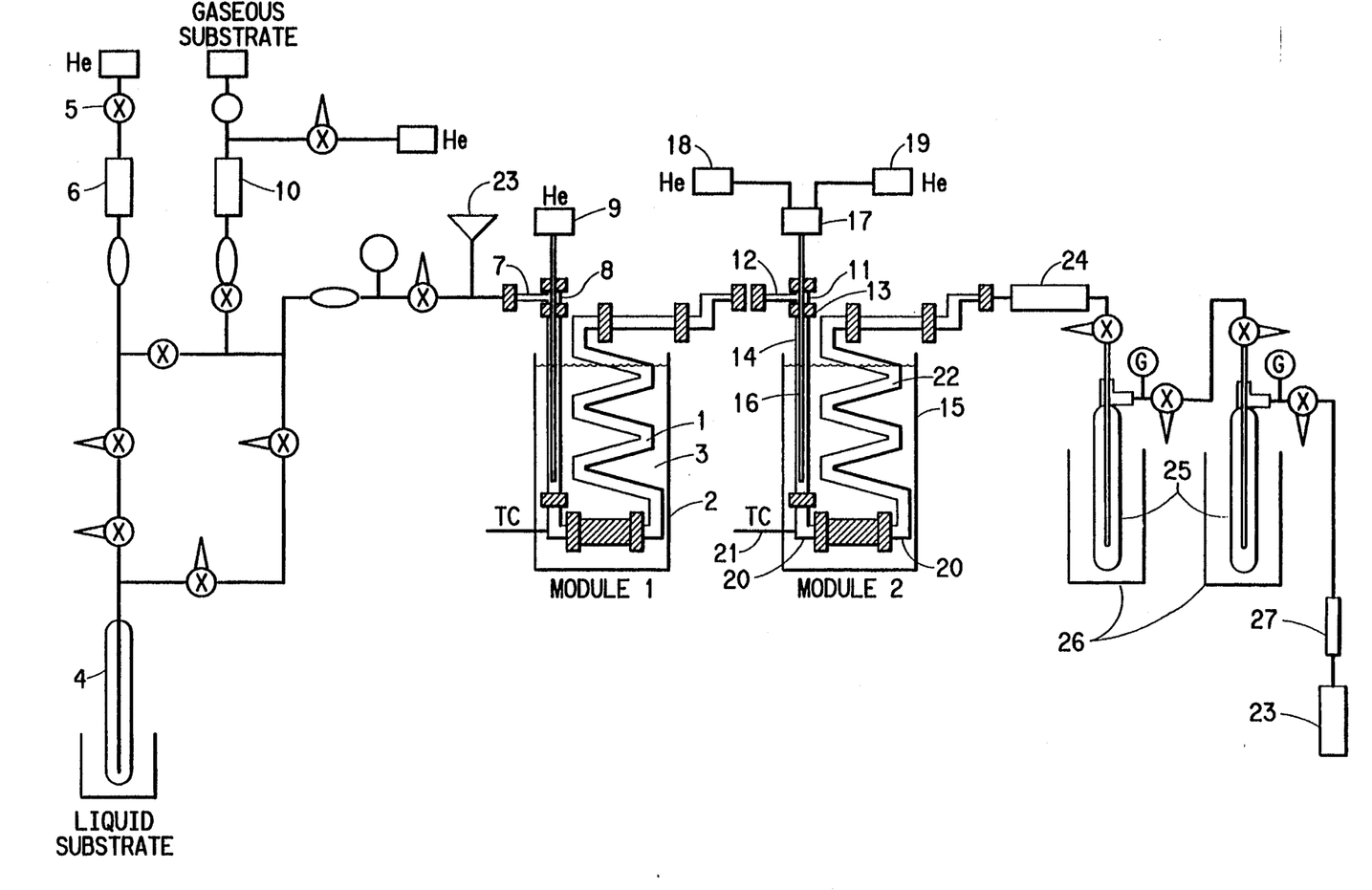

The following examples are presented to further illustrate specific embodiments of the present invention. In performing these examples, the vapor phase fluorination was carried out in a stainless steel reactor located in a well-ventilated laboratory fume hood. A schematic diagram of the reactor is presented in the Figure. The reactor consisted of; (i) a source of substrate to be fluorinated and carrier gas, (ii) a thermostatted coil to bring the substrate and carrier gas to the desired temperature, (iii) a source of a fluorine-carrier gas mixture, (iv) a fluorination zone, (v) product collection trap, and (vi) a means of scrubbing unreacted fluorine.

The thermostatted coil 1 consisted of 148 inches of $\frac{3}{8}$ inch stainless steel tubing (volume ca. 270 mL); this coil 1 is referred to as "Module 1" in the Examples. The coil rested in a 6 liter stainless steel dewar 2 filled with a heat transfer medium 3 to maintain the reactor temperature at desired levels. "FREON" 11, $CFCl_3$, was used for low temperature reactions (<25° C.) with dry ice added to attain low temperatures; "KRYTOX" 143AC, a highly stable perfluoropolyether oil, was used for higher temperature work. The oil was heated by a 750 watt 120 volt immersion heater connected to a variac (not shown).

Liquid substrates were introduced to the reactor by passing a measured flow of helium through a 150 mL thermostatted cylinder 4 of the liquid typically held at 15° C. The helium flow was measured and controlled by means of a needle valve 5 and a rotometer 6. The stream of substrate vapor and helium was directed into the thermostatted coil 1 at the branch arm 7 of a $\frac{3}{8}$ inch tee connection 8 at the top of the coil. The straight run of the tee was fed by another source of helium 9 which was controlled by an electronic flow controller/flow meter. This independent helium stream served as a means of diluting the reaction or adjusting the residence time of the substrate in the reactor. If the substrate was a gas at ambient conditions, it was fed into the thermostatted coil (Module 1) as the pure or helium-diluted vapor by means of a rotometer 10. If a chemical initiator was employed in the fluorination, it was premixed with the substrate at the desired concentration and this mixture was fed to the reactor.

The inlet of the fluorination reactor consisted of a $\frac{3}{8}$ inch tee connection 11. The fluorination zone is referred to as "Module 2" in the Examples. The helium-substrate mixture from the thermostatted coil 1 (Module 1) was connected to this tee at the branch run 12. The bottom of the straight run of the tee 13 was connected to a 10 inch length of $\frac{3}{8}$ inch tubing 14 which extended into another 6 liter steel dewar 15 filled with a heat exchange medium as detailed above for Module 1. Positioned inside of the $\frac{3}{8}$ inch tube 14 was a $\frac{3}{8}$ inch o.d. $\times$4 inch long 0.5 micron porosity "MONEL" tube 16. The lower end of the tube was sealed and the upper end was silver-soldered onto a length of $\frac{1}{4}$ inch stainless steel tubing which extended through the straight run of the $\frac{3}{8}$ inch tee connection. A source of fluorine was connected to this $\frac{1}{4}$ inch tube. Typically in this work the fluorine 18 was diluted with helium in a mixing cylinder 17 which consisted of a 2 inch i.d. $\times$4 inch long stainless steel pipe with $\frac{1}{4}$ inch fittings at each end. The pipe was packed with copper turnings. The mixing chamber was fed by independent streams of electronically-controlled and -measured flows of 100% fluorine 18 and 100% dry helium 19. The substrate was thus introduced into the reactor within the 10 inch length of steel tubing 14 below the $\frac{3}{8}$ inch tee connection and outside of the porous inner tube 16. The fluorine-helium mixture diffused out of the porous inner tube and mixed with the substrate in this zone of the reactor. The net effect of this configuration was that a mixture of fluorine and helium was delivered into the reactor over an extended length rather through a point source.

The bottom of the reactor was approximately 5 inches long and consisted of two 1 inch elbow fittings 20 connected together. This portion of the reactor was packed with copper turnings. A 1/16 inch thermocouple 21 was located in the bottom of the reactor through a fitting silver-soldered into the 1 inch elbow below the porous fluorine inlet tube. The reaction mixture exited the reactor through a second coil 22 of $\frac{3}{8}$ inch stainless steel tubing 102 inches in length (volume ca. 212 mL).

The pressure in the reactor system was monitored by a stainless steel pressure transducer 23 which was placed before the first coil. The transducer was connected to an audible alarm which gave early warning of a blockage in the reactor system. The back pressure in the system was typically about 0.2 psig.

Gases exiting the reactor were directed through a stainless steel cylinder 24 (1 inch i.d., 6 inches long) packed with anhydrous sodium fluoride pellets to trap HF. The HF-free vapors then passed into a product trap. The trap consisted of two 300-mL stainless steel cylinders 25 connected in series and immersed in a steel dewars 26 filled with liquid nitrogen. Uncondensed gases exiting the product trap passed through an HF trap 27 and then into a fluorine scrubber 28. The fluorine scrubber consisted of a stainless steel pipe (4 inches i.d., 2 ft. long) packed with 8–14 mesh activated alumina. Thermocouples taped on the side of the fluorine scrubbers monitored the exothermic reaction between the fluorine and alumina.

EXAMPLES 1-9

The above described reactor was checked for leaks by pressurizing with helium and observing the gauges. Helium was then purged through the reactor system at a rate of 100 sccm for at least one hour. The temperature of the reactor was adjusted to the desired value. A cylinder containing 1,1,1-trifluoroethane, $CH_3CF_3$ (HFC-143a), was connected to the rotometer which in turn was connected to Module 1 at the $\frac{3}{8}$ inch tee connection.

When the reactor temperature had stabilized, the desired mixture of fluorine and helium was fed through the inner element in Module 2. The helium flow through the thermostatted coil in Module 1 was then set at the desired level. These flows were maintained for 5–10 minutes. The desired flow of HCFC-143a was then fed to the reactor.

At the conclusion of the run, the fluorine and $CH_3CF_3$ flows were shut off. The liquid nitrogen dewar surrounding the first product trap was removed. The reactor was purged with helium at 100 sccm for at least 50 minutes.

The second product trap was isolated from the reactor by closing the inlet and outlet valves, and then disconnecting from the system. The product trap was replaced by a length of copper tubing to minimize exposure of the system to air. While not in use, the reactor was purged with helium at a rate of 40 sccm. The product trap still in the liquid nitrogen dewar, was attached to the vacuum line and evacuated to remove helium. Separately, a 50 mL steel cylinder was with a known pressure of $CCl_2F_2$. The $CCl_2F_2$ was then distilled into the product trap to serve as the internal standard for GC analysis. The product trap was then warmed to room temperature; the total pressure in the cylinder was then brought to 800–900 mmHg with nitrogen.

GC analysis of the gas phase fluorination reaction products were performed on a Hewlett-Packard 5880 Gas Chromatograph using a 6 meter by ⅛ inch stainless steel column packed with 5% "KRYTOX" HMW on 60/80 "CARBOPAK" B. The temperature program was the following:
Initial temperature: 40° C.
Initial time: 7 minutes
Program rate: 16° C./minute
Final temperature: 175° C.
Final time: 20 minutes
The product distribution and reactor conditions are presented in Tables Ia and Ib, respectively.

TABLE Ia

FLUORINATION OF $CH_3CF_3$ (HFC-143a)

| Exa. No. | $Rxn^a$ Temp. °C. | $Mole^a$ Ratio $F_2$/143a | % $Conv^c$ 143a | % Yield 134a | % Yield 125 | % Yield 116 | 134a/$125^e$ Ratio | $Conv^f$ $F_2$ |
|---|---|---|---|---|---|---|---|---|
| 1 | 88 | 2.5 | — | 1.7 | 0.08 | — | 20.1 | — |
| 2 | 90 | 5.0 | 13 | 5.4 | 0.3 | — | 19.7 | — |
| 3 | 90 | 8.9 | 48 | 46.3 | 11.5 | 2.4 | 4.0 | — |
| 4 | 76 | 8.9 | 12 | 2.3 | 0.09 | — | 24.6 | — |
| 5 | 61 | 8.9 | 4.5 | 1.1 | 0.03 | — | 36.6 | — |
| 6 | 91 | 0.67 | 4.2 | 2.0 | 0.29 | — | 7.0 | 3.8 |
| 7 | 120 | 0.63 | 28.7 | 20.8 | 2.7 | — | 7.7 | 41.8 |
| 8 | 150 | 0.63 | 33.4 | 31.1 | 5.1 | — | 6.1 | 66.1 |
| 9 | 183 | 0.63 | 48.9 | 29.5 | 5.4 | 2.5 | 5.5 | 76.3 |

$^a$Temperature in fluorination zone, °C.
$^b$Molar ratio of $F_2$ to HFC-143a fed to the reactor.
$^c$% Conversion of HFC-143a = [(moles HFC-143a added) − (moles HFC-143a recovered)](100)/(moles HFC-143a added)
$^d$Yields based on HFC-143a fed to the reactor.
$^e$Molar ratio of HFC-134a to HFC-125 produced during the reaction.
$^f$% Conversion of $F_2$ = Σ (moles of F in fluorinated products)(100)/ (moles $F_2$ added)

TABLE Ib

FLUORINATION OF $CH_3CF_3$ (HFC-143a)
Reaction Conditions

| Exa. No. | Flow Rate 143a/ $He^a$ | Module 1 $F_2$/He $Flow^b$ | Module 2 $F_2$/He $Flow^b$ | Total Flow $Rate^c$ | % $F_2^d$ | $Res^e$ Time, min | $Rxn^f$ Time, min |
|---|---|---|---|---|---|---|---|
| 1 | 5.6/0 | 0/73 | 14/58 | 151 | 9.3 | 1.41 | 30 |
| 2 | 5.6/0 | 0/59 | 28/48 | 151 | 18.6 | 1.41 | 30 |
| 3 | 5.6/0 | 0/59 | 50/36 | 151 | 33.2 | 1.41 | 30 |
| 4 | 5.6/0 | 0/59 | 50/36 | 151 | 33.2 | 1.41 | 30 |
| 5 | 5.6/0 | 0/59 | 50/36 | 151 | 32.2 | 1.41 | 30 |
| 6 | 5.2/0 | 0/21 | 3.5/31.5 | 61 | 5.7 | 3.46 | 40 |
| 7 | 5.6/0 | 0/21 | 3.5/31.5 | 62 | 5.7 | 3.44 | 35 |
| 8 | 5.6/0 | 0/21 | 3.5/31.5 | 62 | 5.7 | 3.44 | 30 |
| 9 | 5.6/0 | 0/21 | 3.5/31.5 | 62 | 5.7 | 3.44 | 30 |

$^a$Flow rates (in sccm) of HFC-143a and helium in substrate feed line.
$^b$Flow rates (in sccm) of fluorine and helium fed to reactor modules.
$^c$Total flow rate (in sccm at ambient temperature) of gases fed to the reactor.
$^d$% $F_2$ = [(flow rate of $F_2$)(100)]/(total gas flow rate).
$^e$Residence time in fluorination zone (min) = [reactor volume (mL)]/(total flow rate (sccm)).
$^f$Duration of fluorination run.

EXAMPLES 10–16

Using the reactor previously described and repeating the procedure of Examples 1–9, a series of seven additional fluorinations of 1,1,1-trifluoroethane were performed. These specific runs were intended to demonstrate the concept of using a chemical initiator during the vapor phase fluorination of 1,1,1-trifluoroethane. Thus after performing a fluorination run in a manner analogous to Examples 1–9, one or more additional runs at identical conditions except for the presence of vinylidene fluoride initiator in the reactor feed stream along with the $CH_3CF_3$ were performed. The resulting data and reaction conditions associated with the respective runs are presented in Tables IIa and IIb.

TABLE IIa

VINYLIDENE FLUORIDE-INITIATED FLUORINATION OF $CH_3CF_3$ (HFC-143a)

| Exa. No. | $Rxn^a$ Temp | Eq.$^b$ $F_2$ | Mole % $VF_2^c$ | % $Conv^d$ 143a | % $Conv^e$ $F_2$ | Yield$^f$ 134a | 134a/ $125^g$ Ratio |
|---|---|---|---|---|---|---|---|
| 10 | 60 | 1.35 | — | 9.2 | — | 6.4 | — |
| 11 | 61 | 1.35 | 1 | 14.5 | — | 60.6 | 9.8 |
| 12 | 91 | 0.67 | — | 4.2 | 3.8 | 47.2 | 7.0 |
| 13 | 90 | 0.67 | 1 | 26.7 | 25.7 | 69.9 | 5.8 |
| 14 | 90 | 0.67 | 4 | 44.0 | 54.5 | 54.2 | 4.9 |
| 15 | 119 | 0.67 | — | 18.6 | 37.1 | — | 3.1 |
| 16 | 118 | 0.67 | 1 | 48.8 | 63.0 | 56.1 | 3.7 |

$^a$Temperature inside reactor, °C.
$^b$Moles of $F_2$ fed to reactor per mole of HFC-143a.
$^c$Mole % of vinylidene fluoride initiator co-fed to reactor with HFC-143a.
$^d$% Conversion of HFC-143a = [(moles HFC-143a added) − (moles HFC-143a recovered)](100)/(moles HFC-143a added).
$^e$% Conversion of $F_2$ = [ Σ(moles of F in fluorinated products)](100)/(moles $F_2$ added)
$^f$% Yield of HFC-134a based on the sum of HFC-143a and vinylidene fluoride converted during the reaction.
$^g$Molar ratio of HFC-134a to HFC-125 produced during the reaction.

TABLE IIb

VINYLIDENE FLUORIDE-INITIATED FLUORINATION OF $CH_3CF_3$ (HFC-143a)
Reaction Conditions

| Exa. No. | Flow Rate 143a/ $He^a$ | Module 1 $F_2$/He $Flow^b$ | Module 2 $F_2$/He $Flow^b$ | Total Flow $Rate^c$ | % $F_2^d$ | $Res^e$ Time, min | $Rxn^f$ Time, min |
|---|---|---|---|---|---|---|---|
| 10 | 5.2/0 | 0/21 | 7/28 | 61 | 11.4 | 3.46 | 30 |
| 11 | 5.2/0 | 0/21 | 7/28 | 61 | 11.4 | 3.46 | 30 |
| 12 | 5.2/0 | 0/21 | 3.5/31.5 | 61 | 5.7 | 3.46 | 40 |
| 13 | 5.2/0 | 0/21 | 3.5/31.5 | 61 | 5.7 | 3.46 | 30 |
| 14 | 5.5/0 | 0/21 | 3.5/31.5 | 62 | 5.7 | 3.46 | 30 |
| 15 | 5.2/0 | 0/21 | 3.5/31.5 | 61 | 5.7 | 3.46 | 30 |

TABLE IIb-continued

VINYLIDENE FLUORIDE-INITIATED FLUORINATION OF CH₃CF₃ (HFC-143a)
Reaction Conditions

| Exa. No. | Flow Rate 143a/He[a] | Module 1 F₂/He Flow[b] | Module 2 F₂/He Flow[b] | Total Flow Rate[c] | % F₂[d] | Res[e] Time, min | Rxn[f] Time, min |
|---|---|---|---|---|---|---|---|
| 16 | 5.2/0 | 0/21 | 3.5/31.5 | 61 | 5.7 | 3.46 | 30 |

[a]Flow rates (in sccm) of HFC-143a and helium in substrate feed line.
[b]Flow rates (in sccm) of fluorine and helium fed to reactor modules.
[c]Total flow rate (in sccm at ambient temperature) of gases fed to the reactor.
[d]% F₂ = [(flow rate of F₂)(100)]/(total gas flow rate).
[e]Residence time in fluorination zone (min) = [reactor volume (mL)]/(total flow rate (sccm)).
[f]Duration of fluorination run.

EXAMPLES 17–24

In a manner analogous to the previous Examples a series of eight additional fluorinations of 1,1,1-trifluoroethane were performed using various alternative initiators as well as light were performed. For Examples 17, 18 and 24, the thermostatted coil (Module 1) was converted to an additional fluorination zone with the substrate and fluorine inlet set up in the same way as described for Module 2 above. In Example 24, Module 1 was converted to a photochemical reactor by replacing the ⅝ inch outer reactor tube which surrounds the inner, porous fluorine inlet tube with a ⅝ inch o.d. (9/16 inch i.d.) FEP tube. For the photo-initiated reaction, the stainless steel Dewar flask filled with the heat transfer medium was removed and a 275 watt sunlamp was positioned ½ inch from the FEP tube during the reaction. The resulting data and reaction conditions associated with the respective runs are presented in Tables IIIa and IIIb.

TABLE IIIa

COMPARISON OF INITIATORS FOR CH₃CF₃ (HFC-143a) FLUORINATION
Reaction Temperature 90° C.
0.67 equivalents F₂ fed to reactor

| Exa. No. | Init(%)[a] | % Conv[b] 143a | % Conv[c] F₂ | Yield[d] 134a | 134a/125[e] Ratio |
|---|---|---|---|---|---|
| 17 | C₂H₄(1) | 38.7 | 51.7 | 65.2 | 5.27 |
| 18 | C₂H₄(2) | 46.2 | 56.9 | 55.4 | 4.27 |
| 19 | C₂H₆(1) | 30.5 | 31.9 | 55.4 | 6.55 |
| 20 | CH₃Cl(1) | 27.0 | 29.4 | 54.6 | 4.44 |
| 21 | CF₂HCFH₂(1) | 15.4 | 2.3 | 7.7 | 7.97 |
| 22 | CF₃I(1) | 15.1 | 13.5 | 79.7 | 14.7 |
| 23 | CF₃I(4) | 26.6 | 28.3 | 60.2 | 7.85 |
| 24 | light | 28.5 | 45.5 | 50.2 | 3.97 |

[a]Initiator present in HFC-143a feed; mole % of initiator given in parentheses.
[b]% Conversion of HFC-143a = [(moles HFC-143a added) − (moles HFC-143a recovered)](100)/(moles HFC-143a added).
[c]% Conversion of F₂ = [ Σ(moles of F₂ in fluorinated products)](100)/(moles F₂ added).
[d]% Yield of HFC-134a based on HFC 143a converted.
[e]Molar ratio of HFC-134a to HFC-125 produced during reaction.
[f]1 Mole % C₂H₄ added with HFC-143a via substrate feed line and 1 mole % C₂H₄ added with helium in Module 2.

TABLE IIIb

COMPARISON OF INITIATORS FOR CH₃CF₃ (HFC-143a) FLUORINATION
Reaction Conditions
Reaction Temperature 90° C.
0.67 equivalents F₂ fed to reactor

| Exa. No. | Flow Rate 143a/He[a] | Module 1 F₂/He Flow[b] | Module 2 F₂/He Flow[b] | Total Flow Rate[c] | % F₂[d] | Res[e] Time, min | Rxn[f] Time, min |
|---|---|---|---|---|---|---|---|
| 17 | 5.1/0 | 3.5/47.5 | 0/5 | 56 | 6.2 | 4.81 | 30 |
| 18 | 5.1/0 | 3.5/47 | 0/5.5 | 56 | 6.3 | 4.86 | 30 |
| 19 | 5.2/0 | 0/21 | 3.5/31.5 | 61 | 5.7 | 3.46 | 30 |
| 20 | 5.0/0 | 0/21 | 3.5/31.5 | 61 | 5.7 | 3.46 | 30 |
| 21 | 5.2/0 | 0/21 | 3.5/31.5 | 61 | 5.7 | 3.46 | 30 |
| 22 | 5.2/0 | 0/21 | 3.5/31.5 | 61 | 5.7 | 3.46 | 30 |
| 23 | 5.2/0 | 0/21 | 3.5/31.5 | 61 | 5.7 | 3.46 | 30 |
| 24 | 5.0/0 | 3.5/21 | 0/31.5 | 30 | 11.9 | 9.15 | 32 |

[a]Flow rates (in sccm) of HFC-143a and helium in substrate feed line.
[b]Flow rates (in sccm) of fluorine and helium fed to the reactor modules.
[c]Total flow rate (in sccm at ambient temperature) of gases in the fluorination zone.
[d]% F₂ = [(flow rate of F₂)(100)]/(total gas flow rate in fluorination zone).
[e]Residence time in fluorination zone (min) = [reactor volume (mL)]/(total flow rate (sccm)).
[f]Duration of fluorination run.
[g]1 Mole % C₂H₄ added with HFC-143a via substrate feed line and 1 mole % C₂H₄ added with helium in Module 2.

EXAMPLES 25 AND 26

In a manner analogous to the previous Examples 1–6, vinylidene fluoride was substituted for 1,1,1-trifluoroethane and subjected to the vapor phase fluorination using the previously described reactor except the thermostatted coil (Module 1) was converted to an additional fluorination zone with the substrate and fluorine inlet set up in the same way as described for Module 2. The resulting data and reaction conditions are presented in Tables IVa and IVb.

TABLE IVa

FLUORINATION OF VINYLIDENE FLUORIDE

| Exa. No. | Rxn[a] Temp. °C. | Mole[b] Ratio F₂/VF₂ | % Conv[c] VF₂ | % Yield[d] 134a | % Yield[d] 125 | 134a/125[e] Ratio |
|---|---|---|---|---|---|---|
| 25 | −15 | 0.33 | 33 | 33.6 | 4.6 | 7.4 |
| 26 | −15 | 2.00 | 99.5 | 49.4 | 19.9 | 2.5 |

[a]Temperature in fluorination zone, °C.
[b]Molar ratio of F₂ to vinylidene fluoride fed to reactor.
[c]% Conversion of VF₂ = [(moles VF₂ added) − (moles VF₂ unconverted)](100)/(moles VF₂ added).
[d]Yields based on VF₂ converted during the reaction: % Yield = (moles product)(100)/[(moles VF₂ added) − (moles VF₂ recovered)].
[e]Molar ratio of HFC-134a to HFC-125 produced during the reaction.

TABLE IVb

FLUORINATION OF VINYLIDENE FLUORIDE
Reaction Conditions

| Exa. No. | Flow Rate $VF_2$/ $He^a$ | Module 1 $F_2$/He Flow[b] | Module 2 $F_2$/He Flow[b] | Total Flow Rate[c] | % $F_2{}^d$ | Res[e] Time, min | Rxn[f] Time, min |
|---|---|---|---|---|---|---|---|
| 25 | 6/50 | 2/103 | 0/286 | 447 | 0.45 | 1.1 | 30 |
| 26 | 6/50 | 6/103 | 6/143 | 314 | 3.8 | 1.5 | 30 |

[a]Flow rates (in sccm) of vinylidene fluoride and helium in substrate feed line.
[b]Flow rates (in sccm) of $F_2$ and helium fed to reactor modules.
[c]Total flow rate of gases fed to reactor.
[d]% $F_2$ = (flow rate $F_2$)(100)/(total flow rate).
[e]Residence time in fluorination zone (min) = [(reactor volume (mL)]/(total flow rate (sccm)).
[f]Duration of fluorination run (min).

Example 27

In a manner analogous to the previous Examples 1 through 9, 1,1,2-trifluoroethane, $CH_2FCHF_2$ (HFC143), was substituted for 1,1,1-trifluoroethane and subjected to the vapor phase fluorination using the previously described reactor. The resulting data and reaction conditions are presented in Tables Va and Vb.

TABLE Va

FLUORINATION OF $CH_2FCHF_2$ (HFC-143)

| Exa. No. | Rxn[a] Temp, °C. | Mole[b] Ratio $F_2$/143 | % Conv[c] 143 | % Yield[d] 152 | 134 | 134a | 125 |
|---|---|---|---|---|---|---|---|
| 27 | −30 | 1.0 | 78.5 | 0.73 | 39.8 | 14.0 | 11.3 |

[a]Temperature in fluorination zone, °C.
[b]Molar ratio of $F_2$ to HFC-143 fed to reactor.
[c]% Conversion of HFC-143 = [(moles HFC-143 added) − (moles HFC-143 unconverted)](100)/(moles HFC-143 added).
[d]Yields based on HFC-143 converted during the reaction: % Yield = (moles product)(100)/[(moles HFC-143 added) − (moles HFC-143 recovered)].

TABLE Vb

FLUORINATION OF $CH_2FCHF_2$ (HFC-143)
Reaction Conditions

| Exa. No. | Flow Rate 143/ $He^a$ | Module 1 $F_2$/He Flow[b] | Module 2 $F_2$/He Flow[b] | Total Flow Rate[c] | % $F_2{}^d$ | Res[e] Time, min | Rxn[f] Time, min |
|---|---|---|---|---|---|---|---|
| 27 | 5/13 | 0/130 | 5/143 | 296 | 3.4 | 0.72 | 30 |

[a]Flow rates (in sccm) of HFC-143 and helium in substrate feed line.
[b]Flow rates (in sccm) of $F_2$ and helium fed to reactor modules.
[c]Total flow rate (in sccm at ambient temperature) of gases fed to reactor.
[d]% $F_2$ = (flow rate $F_2$) (100)/(total flow rate).
[e]Residence time in fluorination zone (min) = [reactor volume (mL)]/(total flow rate (sccm)).
[f]Duration of fluorination run (min).

EXAMPLES 28 AND 29

In a manner analogous to the previous Examples 1 through 9, ethane was substituted for 1,1,1-trifluoroethane and subjected to the vapor phase fluorination using the previously described reactor. The resulting data and reaction conditions are presented in Tables VIa and VIb.

TABLE VIa

FLUORINATION OF ETHANE

| Exa. No. | Mole[a] Ratio $F_2$/$C_2H_6$ | % Conv. $C_2H_6$ | 161 | 152 | 152a | % Yield[c] 143 | 143a | 134 | 134a | 125 |
|---|---|---|---|---|---|---|---|---|---|---|
| 28 | 2.0 | 99.9 | 10.0 | 39.6 | 8.8 | 11.4 | 0.4 | 0.6 | — | — |
| 29 | 5.0 | 100 | — | 1.4 | — | 12.3 | 4.3 | 26.4 | 13.2 | 21.5 |

[a]Molar ratio of $F_2$ to ethane fed to reactor.
[b]% Conversion of ethane = [(moles ethane added) − (moles ethane unconverted)](100)/(moles ethane added).
[c]Yields based on ethane added to the reactor: % Yield = (moles product)(100)/(moles ethane added).

TABLE VIb

FLUORINATION OF ETHANE
Reaction Conditions

| Exa. No. | Flow[a] Rate $C_2H_6$/ He | Rxn[b] Temp, °C. | Module 1 $F_2$/He Flow[c] | Module 2 $F_2$/He Flow[c] | Total Flow Rate[d] | % $F_2{}^e$ | Res[f] Time, min | Rxn[g] Time, min |
|---|---|---|---|---|---|---|---|---|
| 28 | 5.0/0 | −50 | 0/143 | 10/138 | 296 | 3.4 | 0.72 | 35 |
| 29 | 5.0/0 | −30 | 0/143 | 25/123 | 296 | 8.4 | 0.72 | 30 |

[a]Flow rates (in sccm) of ethane and helium in substrate feed line.
[b]Temperature (°C.) in fluorination zone.
[c]Flow rates (in sccm) of $F_2$ and helium fed to reactor modules.
[d]Total flow rate (in sccm at ambient temperature) of gases fed to reactor.
[e]% $F_2$ = (flow rate $F_2$)(100)/(total flow rate).
[f]Residence time in fluorination zone (min) = [(reactor volume (mL)]/(total flow rate (sccm)).
[g]Duration of fluorination run (min).

EXAMPLES 30 AND 31

In a manner analogous to the previous Examples 1 through 9, pentafluoroethane (HFC-125) was substituted for 1,1,1-trifluoroethane and subjected to the vapor phase fluorination using the previously described reactor. The resulting data and reaction conditions are presented in Tables VIIa and VIIb.

TABLE VIIa

FLUORINATION OF PENTAFLUOROETHANE (HFC-125)

| Exa. No. | Temp, °C. | Mole[b] Ratio $F_2$/125 | Mole %[c] $C_2H_4$ | % Conv[d] $F_2$ | Yield[e] 116 |
|---|---|---|---|---|---|
| 30 | 91 | 0.71 | — | 1.1 | 1.1 |

TABLE VIIa-continued

FLUORINATION OF PENTAFLUOROETHANE (HFC-125)

| Exa. No. | Temp, °C. | Mole[b] Ratio $F_2$/125 | Mole %[c] $C_2H_4$ | % Conv[d] $F_2$ | Yield[e] 116 |
|---|---|---|---|---|---|
| 31 | 91 | 0.72 | $C_2H_4(1)$ | 40.1 | 39.0 |

[a]Temperature in fluorination module, °C.
[b]Molar ratio of $F_2$ to pentafluoroethane fed to reactor.
[c]Ethylene added as an initiator.
[d]% Conversion of $F_2$ = (moles of $F_2$ in products)(100)/(moles $F_2$ added); in Example 31 this includes the $F_2$ used to produce HFC-134, HFC-134a, and HFC-143 from ethylene.
[e]Yields based on fluorine fed to the reactor.

TABLE VIIb

FLUORINATION OF PENTAFLUOROETHANE (HFC-125)
Reaction Conditions

| Exa. No. | Flow Rate 143/He[a] | Module 1 $F_2$/He Flow[b] | Module 2 $F_2$/He Flow[b] | Total Flow Rate[c] | $F_2$[d] | Res[e] Time, min | Rxn[f] Time, min |
|---|---|---|---|---|---|---|---|
| 30 | 5.0/0 | 0/21 | 3.5/31.5 | 61 | 5.7 | 3.48 | 30 |
| 31 | 4.9/0 | 0/21 | 3.5/31.5 | 61 | 5.7 | 3.48 | 30 |

[a]Flow rates (in sccm) of HFC-143 and helium in substrate feed line.
[b]Flow rates (in sccm) of $F_2$ and helium fed to reactor modules.
[c]Total flow rate (in sccm at ambient temperature) of gases fed to reactor.
[d]% $F_2$ = (flow rate $F_2$) (100)/(total flow rate).
[e]Residence time in fluorination zone (min) = [reactor volume (mL)]/(total flow rate (sccm)).
[f]Duration of fluorination run (min).

Having thus described and exemplified the invention with a certain degree of particularity, it is to be understood that such details are solely for the purpose of illustration, and that many variations can be made without departing from the spirit and scope of the invention. Thus the following claims are not to be interpreted as being unduly limited, but are to be afforded a scope commensurate with the wording of each element of the claims and equivalents thereto.

I claim:

1. A process for preparing hydrofluorocarbons comprising the steps of:
   (a) contacting a compound selected from the group consisting of:
      (i) saturated, partially fluorinated $C_1$ to $C_5$ hydrocarbons wherein said saturated, partially fluorinated hydrocarbon contains fewer fluorine atoms than are to be present in the hydrofluorocarbon to be prepared, and
      (ii) unsaturated, partially fluorinated $C_2$ to $C_5$ hydrocarbons wherein said unsaturated, partially fluorinated hydrocarbon contains fewer fluorine atoms than are to be present in the hydrofluorocarbon to be prepared with an effective amount of fluorine in the vapor phase for sufficient time to produce a hydrofluorocarbon in the presence of an effective amount an initiator; and
   (b) recovering said hydrofluorocarbon produced in step (a).

2. A process of claim 1 wherein said initiator is selected from the group consisting of: $C_1$ to $C_3$ saturated and unsaturated hydrocarbons; $C_1$ to $C_2$ alkyl halides where the halogen is either Cl, Br or I; $C_2$ to $C_3$ halo-substituted olefins where the halogen is either F, Cl, Br or I; $C_1$ to $C_2$ perfluoroalkyl iodides; and partially fluorinated alkanes more reactive toward fluorine than said compound being contacted with an effective amount of fluorine.

3. A process for converting $CH_3CF_3$ to $CH_2FCF_3$ comprising the steps of:
   contacting $CH_3CF_3$ with an effective amount of fluorine in the vapor phase at a temperature from about 60° C. to about 200° C. for sufficient time to fluorinate said $CH_3CF_3$ wherein said contacting of $CH_3CF_3$ with fluorine is in the presence of an inert diluent and wherein said contacting of $CH_3CF_3$ with fluorine in the presence of an inert gaseous diluent is further in the presence of an effective amount of an initiator; and
   recovering $CH_2FCF_3$ as the predominant product and further comprising the optional step of recovering $CHF_2CF_3$ as an additional product.

4. A process of claim 3 wherein the ratio of said fluorine to said $CH_3CF_3$ is from about 0.1 to about 10, 5. A process of claim 4 wherein the temperature is from about 80° to about 180° C.

6. A process of claim 3 wherein said initiator is $CH_2=CF_2$.

7. A process for converting $CH_2FCHF_2$ to $CHF_2CHF_2$, $CH_2FCF_3$, and $CHF_2CF_3$ comprising the steps of:
   (a) contacting $CH_2FCHF_2$ with an effective amount of fluorine in the vapor phase at a temperature from about −70° C. to about 150° C. for sufficient time to fluorinate said $CH_2FCHF_2$, wherein the ratio of said fluorine to said $CH_2FCHF_2$ is from about 0.1 to about 10, wherein said contacting of $CH_2FCHF_2$ with fluorine is in the presence of an inert gaseous diluent and wherein said contacting with fluorine in the presence of an inert gaseous diluent is further in the presence of an effective amount of an initiator; and
   (b) recovering a mixture of $CHF_2CHF_2$, $CH_2FCF_3$, and $CHF_2CF_3$ as product.

8. A process of claim 7 wherein said initiator is $CH_2=CF_2$.

* * * * *